(12) United States Patent
Cho et al.

(10) Patent No.: US 9,017,712 B2
(45) Date of Patent: Apr. 28, 2015

(54) FILLER COMPOSITION FOR TISSUE REINFORCEMENT

(75) Inventors: Il Hwan Cho, Ansan-si (KR); Eui Jin Hwang, Suwon-si (KR); Moo Seok Seo, Siheung-si (KR); Young Soo Park, Seoul (KR); Byung Su Kim, Ansan-si (KR); Sei Kwang Hahn, Pohang-si (KR); Jung Kyu Park, Daejeon (KR); Jun Seok Yeom, Jinju-si (KR); Eun Ju Oh, Busan (KR)

(73) Assignees: Shin Poong Pharmaceutical Co., Ltd., Gyeonggi-do (KR); Postech Academy-Industry Foundation, Gyeongsangbuk-do (KR)

( * ) Notice: Subject to any disclaimer, the term of this patent is extended or adjusted under 35 U.S.C. 154(b) by 0 days.

(21) Appl. No.: 13/809,432

(22) PCT Filed: Jul. 11, 2011

(86) PCT No.: PCT/KR2011/005072
§ 371 (c)(1),
(2), (4) Date: Mar. 8, 2013

(87) PCT Pub. No.: WO2012/008722
PCT Pub. Date: Jan. 19, 2012

(65) Prior Publication Data
US 2013/0203856 A1  Aug. 8, 2013

(30) Foreign Application Priority Data
Jul. 12, 2010  (KR) .................. 10-2010-0067105

(51) Int. Cl.
*A61K 8/73* (2006.01)
*A61Q 19/08* (2006.01)
*A61K 31/167* (2006.01)
*A61L 27/20* (2006.01)
*A61L 27/52* (2006.01)
*C08B 37/08* (2006.01)
*C08J 3/075* (2006.01)
*C08L 5/08* (2006.01)
*A61L 27/54* (2006.01)

(52) U.S. Cl.
CPC ................ *A61K 8/735* (2013.01); *A61L 27/20* (2013.01); *A61L 27/52* (2013.01); *C08B 37/0072* (2013.01); *C08J 3/075* (2013.01); *C08L 5/08* (2013.01); *C08J 2305/08* (2013.01); *A61K 31/167* (2013.01); *A61Q 19/08* (2013.01); *A61L 27/54* (2013.01); *A61L 2300/402* (2013.01); *A61L 2400/06* (2013.01)

(58) Field of Classification Search
CPC ........... A61L 27/20; A61L 27/52; C08L 5/08; C08B 37/0072; C08J 3/075; A61K 8/735; A61K 31/167; A61Q 19/08
See application file for complete search history.

(56) References Cited

U.S. PATENT DOCUMENTS

| | | | |
|---|---|---|---|
| 4,582,865 A | 4/1986 | Balazs et al. | |
| 5,827,937 A | 10/1998 | Ågerup | |
| 6,831,172 B1 * | 12/2004 | Barbucci et al. | ................. 536/53 |
| 7,829,118 B1 * | 11/2010 | Gravett et al. | ................. 424/488 |

FOREIGN PATENT DOCUMENTS

| | | |
|---|---|---|
| JP | 2002-519481 | 7/2002 |
| KR | 1020080026924 | 3/2008 |
| KR | 1020080074260 | 2/2009 |

OTHER PUBLICATIONS

Tezel Journal of Cosmetic and laser Therapy 2008.*
Vercruysse, et al., "Synthesis and in Vitro Degradation of New Polyvalent Hydrazide Cross-Linked Hydrogels of Hyaluronic Acid" Bioconjugate Chem., (1997) vol. 8, pp. 686-694.
Jeon, et al., "Mechanical Properties and Degradation Behaviors of Hyaluronic Acid Hydrogels cross-Linked at Various Cross-Linking Densities" Science Direct (2007) pp. 251-257.
Junseok Yeom, et al., "Effect of Cross-Linking Reagents for Hyaluronic Acid Hydrogel Dermal Fillers on Tissue Augmentation and Regeneration," Bioconjugate Chem., 2010, 240-247.
Xiang Mei Yan, et al., "Improved synthesis of hyaluronic acid hydrogel and its effect on tissue augmentation," J. Biomater Appl, Apr. 28, 2011, 179-186.
Kotaro, Yoshimura, Progress of Medicine, 2005, vol. 214, No. 2, pp. 145-148.
Levy, Phillip M., et al. "A Split-Face Comparison of a New Hyaluronic Acid Facial Filler Containing Pre-Incorporated Lidocaine Versus a Standard Hyaluronic Acid Facial Filler in the Treatment of Naso-Labial Folds." Journal of Cosmetics and Laser Therapy, 2009, vol. 11, No. 3, pp. 169-173.

* cited by examiner

*Primary Examiner* — Suzanne Ziska
*Assistant Examiner* — Thurman Wheeler
(74) *Attorney, Agent, or Firm* — Clark G. Sullivan; Troutman Sanders LLP

(57) ABSTRACT

The present invention relates to a filler composition for tissue reinforcement, including hyaluronic acid and alkylene diamine crosslinked hydrogel. The filler composition exhibits the positive physical properties required for tissue reinforcement, such as biocompatibility and swelling ability, as well as useful effects in that the same can remain in vivo for a long time.

12 Claims, 5 Drawing Sheets

FILLER COMPOSITION FOR TISSUE REINFORCEMENT

TECHNICAL FIELD

The present invention relates to a biocompatible filler composition useful in tissue augmentation.

BACKGROUND ART

Tissue augmentation such as soft tissue augmentation has been used for the purposes of medicine and beauty care. Such an augmentation may be performed by a surgical method via plastic surgery or a non-surgical method to augment the volume of soft tissue by administering a biocompatible material. For example, as a medical purpose it may be used for facial lipoatrophy shown in HIV-positive patients. Facial lipoatrophy refers to loss of subcutaneous fat in the temple and cheeks, and a very thin appearance. In addition, as a beauty care purpose, it has been used for enlarging the volume of the cheek, lip, breast and hip, and reducing fine and deep wrinkles of the skin.

Hyaluronic acid is a biopolymer wherein repeating units consisting of N-acetyl-D-glucosamine and D-glucuronic acid are linearly linked, and is rich in vitreous humor of the eyeball, synovial fluid of joints, chicken combs and the like. Due to excellent biocompatibility, it has been widely used in the medical and medical instrument fields such as ophthalmic surgical aid, joint function improver, drug delivery material, instillations, wrinkle improver and the like, or in the cosmetics field. However, because hyaluronic acid itself has a short half-life of only a few hours after being administered to the human body to render its application limited, there have been studies to increase the half-life (in vivo persistence) by cross-linking. For example, several documents have reported the synthesis of cross-linked hyaluronic acid derivatives in which compounds having two (2) functional groups such as divinyl sulfone, bis-epoxide, bis-halide, formaldehyde and the like are used as a cross-linking agent, and various products based on such preparation methods are commercially available as a dermal filler for skin soft tissue augmentation. U.S. Pat. No. 4,582,865 discloses a cross-linked hyaluronic acid derivative in which divinyl sulfone (DVS) is used as a cross-linking agent, and a hydrogel form thereof is commercially available under the trademark of Hylaform®. U.S. Pat. No. 5,827,937 discloses a process for preparing a cross-linked hyaluronic acid derivative in which multifunctional epoxy compounds are used as a cross-linking agent. Among them, Restylane®, which is a hydrogel formulation of cross-linked hyaluronic acid prepared by using 1,4-butanediol diglycidyl ether (BDDE) as a cross-linking agent of a multifunctional epoxy compound, received approval from the US FDA and is commercially available globally as a dermal filler for tissue augmentation. All of those products are prepared by linking between the hydroxy group of hyaluronic acid and a cross-linking agent. Although the in vivo persistence of those products is increased as compared with uncross-linked hyaluronic acid, there is a problem in in vivo persistence—the fact that they still degrade within six (6) months.

To resolve the problem of low in vivo persistence of commercially available products, the present applicant filed Korean Patent Application No. 10-2008-0074260 which is directed to a method for preparing a hyaluronic acid-adipic acid dihydrazide (ADH) cross-linked product having high in vivo persistence by using ADH—which is linked to the carboxyl group of hyaluronic acid—as a cross-linking agent, based on the conception that the recognition site of a hyaluronic acid-degrading enzyme is the carboxyl group of hyaluronic acid. Meanwhile, the hyaluronic acid-ADH cross-linked hydrogel shows remarkably high in vivo persistence as compared with commercially available cross-linked hyaluronic acid hydrogels, but there have been problems such as the fact that it is easily broken due to low viscoelasticity, is not well swelled and is not easy to perform tissue correction due to uneven distribution in the tissue. In addition, because hyaluronic acid cross-linked products are prepared by using chemicals—which can be recognized as a foreign substance in the body—as a cross-linking agent, there may a problem wherein immune response is caused by a residual cross-linking agent in case of degrading after being administered to the body. As a result, the amount of cross-linking agent or additive, which can act as a foreign substance, should be minimized in the preparation process. Besides, because it is administered to the body, sterilization should be possible, and physicochemical properties such as viscoelasticity needed for tissue correction should be maintained after sterilization.

As explained above, there is a strong demand for cross-linked hyaluronic acid hydrogel—which has good in vivo persistence and biocompatibility, shows good physical properties such as viscoelasticity and the like even after sterilization, and can be administered to the body tissue by being easily charged into a syringe—to be used as an excellent filler for tissue correction.

PRIOR DOCUMENTS

Patent Documents

U.S. Pat. No. 4,582,865 (disclosed on Apr. 15, 1986)
U.S. Pat. No. 5,827,937 (disclosed on Oct. 27, 1998)
Korean Patent Application No. 10-2008-0074260 (disclosed on Feb. 5, 2009)

DETAILED DESCRIPTION OF THE INVENTION

Technical Problem

The present invention is intended to solve the above problems of the prior art. The purpose of the present invention is to provide a composition comprising a hydrogel of cross-linked hyaluronic acid, which has good in vivo persistence and biocompatibility, and shows good physical properties such as viscoelasticity and the like after sterilization, and can be administered to the body tissue by being easily charged into a syringe to be used as an excellent filler for tissue correction and a method for preparing the same.

Solution to the Problem

To accomplish the above purpose, the present invention provides a filler composition for tissue augmentation comprising the following Formula 1 of hydrogel of hyaluronic acid cross-linked with alkylene diamine.

$$[HA]_m\text{-C(O)}\text{—NH}\text{—R1-NH}\text{—C(O)-}[HA]_n \qquad \text{[Formula 1]}$$

wherein, HA represents hyaluronic acid excluding one carboxyl group or a salt thereof, R1 represents $C_3$-$C_{10}$ alkylene unsubstituted or substituted with hydroxy, $C_1$-$C_6$ alkyl or $C_1$-$C_6$ alkoxy, and m and n independently are an integer of 10,000 to 4,000,000, preferably 20,000 to 3,000,000.

Preferably, the hydrogel of hyaluronic acid cross-linked with alkylene diamine is comprised in an amount of 1 to 3 (w/w) % based on the total weight of the composition.

Preferably, the composition of the present invention further comprises unmodified (i.e., uncross-linked) hyaluronic acid, and the composition can be charged into a syringe and easily injected to tissues by decreasing extrusion force.

Preferably, the unmodified hyaluronic acid is comprised in an amount of 0.05 to 1 (w/w) % based on the total weight of the composition.

Preferably, the composition of the present invention further comprises lidocaine in addition to the hydrogel of hyaluronic acid cross-linked with alkylene diamine and the unmodified hyaluronic acid to prevent lowering of elasticity after sterilization and show local anesthetic effect.

Preferably, the lidocaine is comprised in an amount of 0.1 to 0.4 (w/w) % based on the total weight of the composition.

The remaining part of the present composition is comprised of a pharmaceutically acceptable carrier such as water, saline and the like.

In the composition of the present invention, the molecular weight of hyaluronic acid is preferably 20,000 to 4,000,000 Dalton (Da).

In the composition of the present invention, alkylene diamine is preferably hexamethylenediamine.

In the composition of the present invention, the hydrogel of hyaluronic acid cross-linked with alkylene diamine is preferably prepared by reacting hyaluronic acid with $C_3$-$C_{10}$ alkylene diamine compound unsubstituted or substituted with hydroxy, $C_1$-$C_6$ alkyl or $C_1$-$C_6$ alkoxy in the presence of a carboxyl-activating agent and a peptide bond catalyst at pH 5.5 to 6.5.

In the composition of the present invention, the cross-linking ratio of the hydrogel of hyaluronic acid cross-linked with alkylene diamine is preferably 5 to 35% (TNBS assay).

In the present specification, the term "augmentation" refers to increase of tissue volume (e.g., tissue enlargement) and/or improvement of tissue function. Therefore, the filler for tissue augmentation according to the present invention may be used for clinically or aesthetically increasing the volume of soft tissue or improving tissue function. Specifically, it may be used for removing or improving wrinkles of the skin, or enlarging the volume of body part such as cheek, lip, breast or hip.

In addition, in the present specification the term "hyaluronic acid" is used to refer to salts or derivatives of hyaluronic acid as well as hyaluronic acid itself. Therefore, hereinafter the used term "hyaluronic acid aqueous solution" includes all of aqueous solution of hyaluronic acid, aqueous solution of salt of hyaluronic acid and a mixed aqueous solution thereof.

In addition, the present invention provides a method for preparing the composition according to the present invention, which comprises the steps of:

(1) reacting hyaluronic acid with $C_3$-$C_{10}$ alkylene diamine compound unsubstituted or substituted with hydroxy, $C_1$-$C_6$ alkyl or $C_1$-$C_6$ alkoxy in the presence of a carboxyl-activating agent and a peptide bond catalyst to prepare a hydrogel of hyaluronic acid cross-linked with alkylene diamine;

(2) homogenizing the prepared hydrogel; and (3) removing unreacted materials.

Preferably, the method of the present invention can prepare a hydrogel of hyaluronic acid cross-linked with alkylene diamine having excellent physical properties such as modulus of elasticity even after sterilization by adding a carboxyl-activating agent and a peptide bond catalyst dissolved in water to a mixture of hyaluronic acid and alkylene diamine compound within 30 minutes.

Preferably, the method of the present invention can prepare a hydrogel of hyaluronic acid cross-linked with alkylene diamine having excellent physical properties such as modulus of elasticity even after sterilization by keeping the reaction system at 30° C. to 50° C. for at least 9 hours without agitation to make hyaluronic acid and alkylene diamine sufficiently and completely cross-linked.

Preferably, the method of the present invention can prepare a hydrogel of hyaluronic acid cross-linked with alkylene diamine having excellent physical properties such as modulus of elasticity, and high biocompatibility even after sterilization with the use of a small amount of a cross-linking agent (alkylene diamine) and catalysts (a carboxyl-activating agent and a peptide bond catalyst) by preparing the hydrogel of hyaluronic acid cross-linked with alkylene diamine at pH 5.5 to 6.5.

Preferably, the method of the present invention can prepare a composition—which is easily charged into a syringe and injected into tissues by showing relatively low extrusion force even after sterilization—by homogenizing the prepared hydrogel via passing through a sieve to obtain a homogenized hydrogel having uniform size and narrow particle size distribution.

Preferably, the method of the present invention can easily remove unreacted materials such as alkylene diamine, a carboxyl-activating agent and a peptide bond catalyst within a short time by precipitating with $C_1$-$C_6$ alcohol aqueous solution and washing with phosphate-buffered saline (PBS) or sodium chloride buffer.

Hereinafter, a hydrogel of hyaluronic acid cross-linked with alkylene diamine according to the present invention, a composition comprising the same and a method for preparing the same are explained in more detail.

1) Preparation of Hydrogel of Hyaluronic Acid Cross-Linked with Alkylene Diamine A hydrogel of hyaluronic acid cross-linked with alkylene diamine is prepared by reacting hyaluronic acid with alkylene diamine compound in the presence of a carboxyl-activating agent and a peptide bond catalyst.

The molecular weight of the used hyaluronic acid (HA) is 10,000 to 4,000,000 Da, more preferably 20,000 to 3,000,000 Da. The degradation rate of the prepared cross-linked hydrogel may be controlled by adjusting the molecular weight or concentration of HA. Usually, if initial concentration of HA is higher, the cross-linking ratio of the prepared cross-linked hydrogel is higher. According to this, the cross-linked hydrogel shows a low degradation rate in the body. Preferably, HA may be used in the concentration of 1 to 3.5 (w/w) %, more preferably 3 (w/w) %. If the concentration is less than 1 (w/w) %, it may be difficult to obtain the desired degradation rate in the body. If the concentration is greater than 3.5 (w/w) %, the prepared hydrogel may be dry and easily break.

The alkylene diamine compound is $C_3$-$C_{10}$ alkylene diamine compound unsubstituted or substituted with hydroxy, $C_1$-$C_6$ alkyl or $C_1$-$C_6$ alkoxy, preferably $C_3$-$C_7$ alkylene diamine, more preferably $C_4$-$C_6$ alkylene diamine, and most preferably $C_6$ alkylene diamine (hexamethylenediamine). The alkylene diamine compound may be used as 3.5 to 80 mol %, preferably 10 to 30 mol %, and most preferably 10 to 25 mol % based on the repeating unit of hyaluronic acid.

As the carboxyl-activating agent, carbodiimide of water-soluble carbodiimide—e.g., 1-alkyl-3-(3-dimethylaminopropyl) carbodiimides such as 1-ethyl-3-(3-dimethylaminopropyl) carbodiimide (EDC), 1-alkyl-3-(3-(trimethylammonio)propyl) carbodiimides such as 1-ethyl-3-(3-(trimethylammonio)propyl) carbodiimide (ETC), and 1-cycloalkyl-3-(2-morpholinoethyl) carbodiimides such as 1-cyclohexyl-3-(2-morpholinoethyl) carbodiimide (CMC), more preferably 1-ethyl-3-(3-dimethylaminopropyl) carbodiimide (EDC)—may be used. The carboxyl-activating agent is preferably used in the molar ratio of 1 to 5 times per 1 mole of hyaluronic acid.

As the peptide bond catalyst, for example, 1-hydroxybenzotriazole (HOBt), 3,4-dihydro-3-hydroxy-4-oxo-1,2,3-benzotriazine (HOOBt), 1-hydroxy-7-azabenzotriazole (HOAt), Sulfo-N-hydroxysulfosuccinimide (Sulfo-NHS), O-(1H-benzotriazole-1-yl)-N,N,N',N'-tetramethyluronium tetrafluoroborate (TBTU), more preferably 1-hydroxybenzotriazole (HOBt) may be used. The peptide bond catalyst is preferably used in the molar ratio of 1 to 5 times per 1 mole of hyaluronic acid.

Preferably, the hyaluronic acid-hexamethylenediamine cross-linked product prepared by using hexamethylenediamine (HMDA) as an alkylene diamine compound is represented in FIG. 1. As can be seen from FIG. 1, the carboxyl group of hyaluronic acid and the amine group of alkylene diamine compound are cross-linked via amide bond in the presence of a carboxyl-activating agent and a peptide bond catalyst. Intermolecular or intramolecular cross-link may occur. The carboxyl group of hyaluronic acid is an important group which is involved in recognition of hyaluronic acid by hyaluronidase, a hyaluronic acid-degrading enzyme. In the hydrogel of hyaluronic acid cross-linked with alkylene diamine according to the present invention, the carboxyl group of hyaluronic acid is used in cross-linking, so that in vivo persistence can be increased by minimizing the degradation of hyaluronic acid by degrading enzymes after being administered to the body. In addition, (-) charge of carboxyl group affects the physical properties of hydrogel such as swellability, which largely contributes to tissue augmentation.

The above cross-linking reaction is usually carried out in water. Hyaluronic acid, alkylene diamine compound, a carboxyl activating agent and a peptide bond catalyst may be dissolved in water, respectively, and then mixed, or a solution in which hyaluronic acid and alkylene diamine compound may be mixed with a solution in which a carboxyl-activating agent and a peptide bond catalyst are dissolved. Specifically, in case of EDC used as a carboxyl-activating agent, it may be changed to N-ethyl-N-(3-dimethylaminopropyl) urea (EDU) in a weak acidic condition. As a result, if the addition of EDC dissolved in water to a mixture of hyaluronic acid and alkylene diamine to be cross-linked is delayed, the deterioration of physical properties of the prepared cross-linked product—such as lowering the modulus of elasticity of composition after sterilization—may occur. Preferably, the time required from dissolution to addition may be within 10 to 30 minutes, more preferably within 10 to 20 minutes.

In addition, the reaction temperature may be maintained at 30 to 50° C., more preferably 43 to 45° C. At the above temperature, a hydrogelation reaction efficiently progresses, so that hydrogel usually forms within 30 minutes. Furthermore, a hydrogel having good viscoelasticity may be prepared by keeping at the above temperature for at least 9 hours. At this time, keeping without agitation is preferable. As the additional reaction time is increased, physical properties such as viscoelasticity are increased. However, there is little change in physical properties such as viscoelasticity of the prepared hydrogel for more than 9 hours.

In addition, the cross-linking rate of the prepared cross-linked hydrogel may be changed according to pH at the time of preparation, which is a result of the change of physical properties. The pH may be adjusted by the addition of NaOH aqueous solution to a reaction solution, and preferably may be 5.5 to 6.5, more preferably 6.0 to 6.3. Specifically, by means of adjusting pH to 5.5 to 6.5, a hydrogel of hyaluronic acid cross-linked with alkylene diamine—which has good physical properties such as viscoelasticity, and has no change in physicochemical properties such as viscoelasticity even after sterilization—may be prepared even if a relatively small amount of a cross-linking agent (e.g., hexamethylenediamine) and a reaction catalyst (e.g., a carboxyl-activating agent such as EDC and a peptide bond catalyst such as HOBt) are used. A hydrogel prepared in an acidic environment of lower than pH 5.5 shows relatively low modulus of elasticity (G'), and elasticity may be further lowered at the time of sterilization.

2) Homogenization of Hydrogel

The prepared hydrogel is rendered into uniform particles by passing through a sieve or by using a homogenizer. Specifically, it is preferable to employ homogenization by using a sieve to obtain a hydrogel having narrow particle size distribution and low extrusion Force.

3) Removal of Unreacted Materials

After cross-linking reaction, unreacted materials may be removed by dialyzing with a dialysis membrane in PBS for 24 hours to 3 days, or by using ethanol aqueous solution and/or buffer to below the detection limit (2 ppm). However, a catalyst such as HOBt having a tendency of more easily dissolving in organic solvent is not well purified by a dialysis method using a dialysis membrane and PBS, but is easily removed by using ethanol aqueous solution and/or buffer to below the detection limit. At this time, buffer may be preferably PBS solution or sodium chloride (NaCl) solution, more preferably sodium chloride (NaCl) solution. If the concentration of used NaCl is higher, purification is easier, and the concentration of NaCl is preferably 0.5 to 1.5%, most preferably 1 to 1.3%. In addition, in the case of adding ethanol aqueous solution—e.g., 80% ethanol aqueous solution—hydrogel particles are formed as a precipitate, and unreacted materials are easily removed at this step. The precipitated hydrogel may be dried with nitrogen gas to powdery form, and the powdery hydrogel may be rehydrated with a physiologically acceptable aqueous solution. At this time, the physiologically acceptable aqueous solution is preferably PBS or saline, and 20 to 30 times (volume ratio) of the physiologically acceptable aqueous solution based on the hyaluronic acid-alkylene diamine cross-linked hydrogel powder may be used for rehydration.

A hyaluronic acid-alkylene diamine cross-linked hydrogel of the present invention has the cross-linking ratio of 5 to 35%, preferably 10 to 20%. If the cross-linking ratio is less than 5%, it may be difficult to obtain the desired in vivo persistence since the hydrogel is easily degraded by hyaluronidase, a hyaluronic acid-degrading enzyme, by increasing the ratio of unreacted —COOH group which is not involved in cross-linking of hyaluronic acid. If the cross-linking ratio is greater than 35%, it may be difficult to show swellability of hydrogel and viscoelasticity to the extent of being useful for tissue augmentation, and biocompatibility is low—such as high risk of inflammation reaction due to high content of the remaining cross-linking agent after degradation in the body. In addition, if the cross-linking ratio of hydrogel is low, physical properties such as viscoelasticity after sterilization may be deteriorated.

The cross-linking ratio of the hyaluronic acid-alkylene diamine cross-linked product of the present invention refers to the percentage of the content of hyaluronic acid which participates in cross-linking to overall content of hyaluronic acid. The cross-linking rate may be controlled by adjusting the use ratio of alkylene diamine used as a cross-linking agent to overall hyaluronic acid or adjusting pH at the time of preparation. The measurement of the cross-linking rate can be easily carried out by known methods in the art—e.g., NMR analysis and TNBS assay (Habeeb, A. F. S. A., *Determination of free amino groups in proteins by trinitrobenzenesulfonic acid*. Anal. Biochem., 1966, 14: pp. 328-333).

The above hydrogel comprised of hyaluronic acid-alkylene diamine cross-linked product of the present invention shows a remarkably low degrading rate as compared with HA-divinyl sulfone (DVS) cross-linked hydrogel in which DVS is used as a cross-linking agent, and shows about twice the swellability as compared with HA-adipic acid dihydrazide (ADH) cross-linked hydrogel in which ADH is used as a cross-linking agent.

A filler composition for tissue augmentation of the present invention preferably comprises 1 to 3 (w/w) %, more preferably 1.8 to 2.4 w/w (%) of the above hydrogel of hyaluronic acid cross-linked with alkylene diamine based on the total weight of the composition. If the content of the hydrogel is less than 1 (w/w) %, the prepared composition may not have the desired in vivo persistence and extrusion force. If the content of the hydrogel is greater than 3 (w/w) %, it may be difficult to inject into tissues due to too-high extrusion force of the composition.

Meanwhile, the composition of the present invention may further comprise unmodified (i.e., uncross-linked) hyaluronic acid in addition to the hydrogel of hyaluronic acid cross-linked with alkylene diamine. Unmodified HA is usually the same as that used in the preparation of the hyaluronic acid-alkylene diamine cross-linked hydrogel. Unmodified HA acts as a lubricant to decrease extrusion force of the composition, so that when the composition is charged into a syringe it can be injected into tissues with low pressure. Preferably, the unmodified hyaluronic acid is comprised in an amount of 0.05 to 1 (w/w) %, more preferably 0.1 to 0.4 w/w (%) based on the total weight of the composition. If the content of the unmodified hyaluronic acid is less than 0.05 (w/w) %, it may be difficult to obtain the desired extrusion force. If the content of the unmodified hyaluronic acid is greater than 1 (w/w) %, the composition may be continuously ejected little by little even with one pressure due to excessive lowering of extrusion force, and physical properties may deteriorate such as excessive lowering of modulus of elasticity after sterilization.

In addition, the composition of the present invention may further comprise a local anesthetic such as lidocaine in addition to the hydrogel of hyaluronic acid cross-linked with alkylene diamine and the unmodified hyaluronic acid to show better physical properties after sterilization as well as anesthetic effect. In case of mixing the unmodified hyaluronic acid with the hydrogel of hyaluronic acid cross-linked with alkylene diamine, extrusion force of the composition is lowered, but modulus of elasticity (G') of the composition after sterilization is lower than that of the hydrogel in which the unmodified hyaluronic acid is not mixed. However, if lidocaine is mixed, modulus of elasticity after sterilization increases 1.28 times or more without affecting extrusion force of the composition. That is, by mixing unmodified HA with the hydrogel of hyaluronic acid cross-linked with alkylene diamine of the present invention, extrusion force of the composition can be lowered, and lowering of elasticity after sterilization by unmodified HA can be prevented by mixing lidocaine. Preferably, lidocaine is comprised in an amount of 0.1 to 0.4 (w/w) %, more preferably 0.2 to 0.3 w/w (%) based on the total weight of the composition. If the content of lidocaine is less than 0.1 (w/w) %, it may be difficult to sufficiently compensate for lowering of elasticity after sterilization due to unmodified hyaluronic acid. If the content of lidocaine is greater than 0.4 (w/w) %, it may cause unpleasantness by overly anesthetizing tissues.

The remaining part of the composition is comprised of a pharmaceutically acceptable carrier such as water, saline and the like.

Effects of the Invention

The composition using the hydrogel of hyaluronic acid cross-linked with alkylene diamine according to the present invention has good physical properties needed for tissue augmentation and shows an advantageous effect of decreasing the number of times of being exchanged due to excellent in vivo persistence. In addition, the composition further comprising unmodified hyaluronic acid and a local anesthetic shows advantages in that it can be easily used after sterilization since deterioration of physical properties needed for tissue augmentation after sterilization such as lowering of modulus of elasticity does not occur, and can be easily charged into a syringe and injected into tissues due to low extrusion force, in addition to the above effects.

Figure 1:
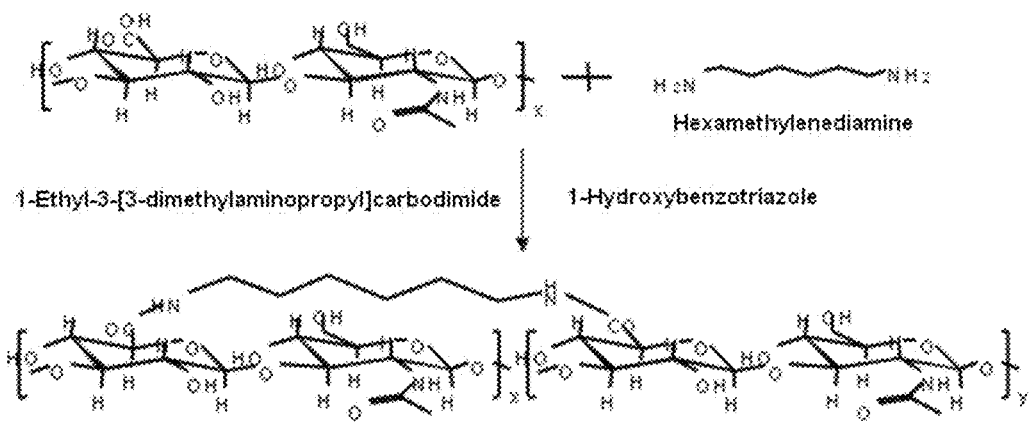
FIG. 1 is a scheme of the synthesis procedure of the HA-HMDA cross-linked product of the present invention and synthesized cross-linked product structure.

HA-HMDA hydrogel of Example 11 treated group, E: epidermis, D: dermis, H: hypoderm).

MODES FOR CARRYING OUT THE INVENTION

Example 1

Preparation of Hyaluronic Acid-Hexamethylenediamine (HA-HMDA) Cross-Linked Hydrogel of the Present Invention Hyaluronic acid (HA, manufacturer: Lifecore Co.) having molecular weight of about 230 kDa was completely dissolved in distilled water at the concentration of 1 (w/w) %, and hexamethylenediamine (HMDA) was then added thereto for cross-linking by reaction with the carboxyl group of HA. HMDA was added as 72 mol % of the repeating unit of HA. 1-Ethyl-3-(3-dimethylaminopropyl)carbodiimide (EDC), a carboxyl-activating agent, and 1-hydroxybenzotriazole (HOBt) were dissolved in distilled water at 1.4 times the amount of HA repeating unit, and were then added to the above mixed solution of HA and HMDA. For complete cross-linking reaction of HA-HMDA cross-linked product, the above mixed solution was reacted at 37° C. for 1 hour. The pH of the solution was 5.0-5.5. The prepared HA-HMDA hydrogel was then sealed with a pre-washed dialysis membrane (molecular weight cut-off of 7 kDa) and dialyzed with 0.01 M PBS (phosphate-buffered saline, pH 7.4) for 24 hours to remove residual EDC, HOBt and HMDA. The cross-linking rate of the prepared HA-HMDA hydrogel was 8-9%.

Example 1-1

Hyaluronic acid (HA, manufacturer: Lifecore Co.) having molecular weight of about 230 kDa was completely dissolved in distilled water at the concentration of 1 (w/w) %, and hexamethylenediamine (HMDA) was then added thereto for cross-linking by reaction with the carboxyl group of HA. HMDA was added as 72 mol % of the repeating unit of HA. 1-Ethyl-3-(3-dimethylaminopropyl)carbodiimide (EDC), a carboxyl-activating agent, and 1-hydroxybenzotriazole (HOBt) were dissolved in distilled water at 1.4 times the amount of HA repeating unit, and were then added to the above mixed solution of HA and HMDA. For complete cross-linking reaction of HA-HMDA cross-linked product, the above mixed solution was reacted at 37° C. for 1 hour. The pH of the solution was 5.0-5.5. The prepared HA-HMDA hydrogel was then pulverized and passed through a 200 µm pore size sieve to obtain a homogenized hydrogel. By addition of 80% ethanol, hydrogel powder was obtained as a precipitate, and 100 times volume of 1.3% NaCl solution was added thereto and agitated for 1 hour. 80% ethanol was again added to obtain a precipitate, and then the obtained hydrogel precipitate was added to 100% ethanol for 10 minutes and dried under reduced pressure at 40° C. for 12 hours to remove residual EDC, HOBt and HMDA. The cross-linking rate of the prepared HA-HMDA hydrogel was 8-9%.

Example 1-2

An HA-HMDA hydrogel was prepared according to the same method as Example 1-1 except that HMDA was added as 25 mol % of the repeating unit of HA. The cross-linking rate of the prepared HA-HMDA hydrogel was 6-7%.

Example 2

Preparation of Hyaluronic Acid-Hexamethylenediamine (HA-HMDA) Cross-Linked Hydrogel of the Present Invention An HA-HMDA hydrogel was prepared according to the same method as Example 1 except that hyaluronic acid (HA, manufacturer: Lifecore Co.) having molecular weight of about 1,000 kDa was used at the concentration of 1 (w/w) %, and pH of the solution was 5.5-5.9. The cross-linking rate of the prepared HA-HMDA hydrogel was 11-13%.

Example 3

Preparation of Hyaluronic Acid-Hexamethylenediamine (HA-HMDA) Cross-Linked Hydrogel of the Present Invention An HA-HMDA hydrogel was prepared according to the same method as Example 1 except that hyaluronic acid (HA, manufacturer: Lifecore Co.) having molecular weight of about 1,000 kDa was used at the concentration of 1.5 (w/w) %, and HMDA was added as 25 mol % of the repeating unit of HA. The pH of the prepared HA-HMDA hydrogel was 5.0-5.5. The cross-linking rate of the prepared HA-HMDA hydrogel was 11-13%.

Example 4

Preparation of Hyaluronic Acid-Hexamethylenediamine (HA-HMDA) Cross-Linked Hydrogel of the Present Invention Hyaluronic acid (HA, manufacturer: Lifecore Co.) having molecular weight of about 1,000 kDa was completely dissolved in distilled water at the concentration of 3 (w/w) %, and hexamethylenediamine (HMDA) was then added thereto for cross-linking by reaction with the carboxyl group of HA. HMDA was added as 20 mol % of the repeating unit of HA. The pH was adjusted to 6.0-6.5 by adding 0.25 N NaOH aqueous solution. 1-Ethyl-3-(3-dimethylaminopropyl)carbodiimide (EDC), a carboxyl-activating agent, and 1-hydroxybenzotriazole (HOBt) were dissolved in distilled water at 1.0 times the amount of HA repeating unit, and were then added to the above mixed solution of HA and HMDA. The pH was adjusted to 6.0-6.5 by adding 0.25 N NaOH aqueous solution. For complete cross-linking reaction of HA-HMDA cross-linked product, the above mixed solution was reacted at 45° C. for 1 hour. The prepared HA-HMDA hydrogel was then sealed with a pre-washed dialysis membrane (molecular weight cut-off of 7 kDa) and dialyzed with 0.01 M PBS (phosphate-buffered saline, pH 7.4) for 24 hours to remove residual EDC, HOBt and HMDA. The cross-linking rate of the prepared HA-HMDA hydrogel was 10-14%.

Example 4-1

Hyaluronic acid (HA, manufacturer: Lifecore Co.) having molecular weight of about 1,000 kDa was completely dissolved in distilled water at the concentration of 3 (w/w) %, and hexamethylenediamine (HMDA) was then added thereto for cross-linking by reaction with the carboxyl group of HA. HMDA was added as 20 mol % of the repeating unit of HA. The pH was adjusted to 6.0-6.5 by adding 0.25 N NaOH aqueous solution. 1-Ethyl-3-(3-dimethylaminopropyl)carbodiimide (EDC), a carboxyl-activating agent, and 1-hydroxybenzotriazole (HOBt) were dissolved in distilled water at 1.0 times the amount of HA repeating unit, and were then added to the above mixed solution of HA and HMDA. The mixed solution was agitated at 45° C. for 30 minutes, and was then kept at 45° C. for 10 hours without agitation for complete cross-linking reaction of HA-HMDA cross-linked product. The prepared HA-HMDA hydrogel was primarily crushed, and then passed through a 200 nm pore size sieve to obtain homogenized hydrogel. By the addition of 80% ethanol, hydrogel powder was obtained as a precipitate, and 1.3% NaCl solution was then added thereto at 100 times the volume and agitated for 1 hour. 80% ethanol was added again to obtain a precipitate, and the obtained hydrogel precipitate was then added to 100% ethanol for 10 minutes and dried under reduced pressure at 40° C. for 12 hours to remove residual EDC, HOBt and HMDA. By LC analysis, it can be confirmed that unreacted materials are controlled below the detection limit of 2 ppm. The cross-linking rate of the prepared HA-HMDA hydrogel was 10-14%.

Examples 4-2 to 4-4

An HA-HMDA hydrogel was prepared according to the same method as Example 4-1 except that 1-ethyl-3-(3-dimethylaminopropyl)carbodiimide (EDC) and 1-hydroxybenzotriazole (HOBt) were added in distilled water, respectively, agitated for 30, 40 and 60 minutes, and were then added to a mixed solution of HA and HMDA.

Examples 4-5 to 4-8

An HA-HMDA hydrogel was prepared according to the same method as Example 4-1 except that a mixed solution was kept at 45° C. for 3, 5, 7 and 9 hours without agitation.

Example 4-9

An HA-HMDA hydrogel was prepared according to the same method as Example 4-1 except that the hydrogel was homogenized with a homogenizer (T-18 basic, IKA) at 8,000 rpm for 5 minutes instead of passing through a sieve.

Example 4-10

An HA-HMDA hydrogel was prepared according to the same method as Example 4-1 except that the prepared HA-HMDA hydrogel was then sealed with a dialysis membrane (molecular weight cut-off of 7 kDa) and dialyzed with PBS (pH 7.4) for 24 hours.

Example 5

Preparation of Hyaluronic Acid-Hexamethylenediamine (HA-HMDA) Cross-Linked Hydrogel of the Present Invention An HA-HMDA hydrogel was prepared according to the same method as Example 4 except that hyaluronic acid having molecular weight of about 1,000 kDa was used at the concentration of 3 (w/w) %, HMDA was added as 20 mol % of the repeating unit of HA, and the pH was adjusted to 5.5-5.9 by adding 0.25 N NaOH aqueous solution. The cross-linking rate of the prepared HA-HMDA hydrogel was 10-12%.

Example 6

Preparation of Hyaluronic Acid-Hexamethylenediamine (HA-HMDA) Cross-Linked Hydrogel of the Present Invention An HA-HMDA hydrogel was prepared according to the same method as Example 4 except that hyaluronic acid having molecular weight of about 1,000 kDa was used at the concentration of 3 (w/w) %, and HMDA was added as 10 mol % of the repeating unit of HA. The cross-linking rate of the prepared HA-HMDA hydrogel was 5-7%.

Example 7

Preparation of Hyaluronic Acid-Hexamethylenediamine (HA-HMDA) Cross-Linked Hydrogel of the Present Invention An HA-HMDA hydrogel was prepared according to the same method as Example 4 except that hyaluronic acid having molecular weight of about 1,000 kDa was used at the concentration of 3 (w/w) %, and HMDA was added as 40 mol % of the repeating unit of HA. The cross-linking rate of the prepared HA-HMDA hydrogel was 32-35%.

Example 8

Composition Comprising Hyaluronic Acid-Hexamethylenediamine (HA-HMDA) Cross-Linked Hydrogel of the Present Invention 20 mg of the hyaluronic acid-alkylene diamine hydrogel powder prepared and dried according to the method of Example 4-1 was dissolved in 1 ml of PBS (pH 7.4) and agitated for 5 hours to obtain a composition comprising the hydrogel of the present invention.

Example 9

Composition Comprising Hyaluronic Acid-Hexamethylenediamine (HA-HMDA) Cross-Linked Hydrogel of the Present Invention 2 mg of hyaluronic acid (HA) having molecular weight of 1,000 kDa was added to 18 mg of the hyaluronic acid-alkylene diamine hydrogel powder prepared and dried according to the method of Example 4-1. The resultant was dissolved in 1 ml of PBS (pH 7.4) and agitated for 5 hours to obtain a composition comprising the hydrogel of the present invention and unmodified hyaluronic acid.

Example 10

Composition comprising hyaluronic acid-Hexamethylenediamine (HA-HMDA) Cross-Linked Hydrogel of the Present Invention 4 mg of hyaluronic acid (HA) having molecular weight of 1,000 kDa was added to 16 mg of the hyaluronic acid-alkylene diamine hydrogel powder prepared and dried according to the method of Example 4-1. The resultant was dissolved in 1 ml of PBS (pH 7.4) and agitated for 5 hours to obtain a composition comprising the hydrogel of the present invention and unmodified hyaluronic acid.

Example 11

Composition Comprising Hyaluronic Acid-Hexamethylenediamine (HA-HMDA) Cross-Linked Hydrogel of the Present Invention 2 mg of hyaluronic acid (HA) having molecular weight of 1,000 kDa and 3 mg of lidocaine were added to 18 mg of the hyaluronic acid-alkylene diamine hydrogel powder prepared and dried according to the method of Example 4-1. The resultant was dissolved in 1 ml of PBS (pH 7.4) and agitated for 5 hours to obtain a composition comprising the hydrogel of the present invention, unmodified hyaluronic acid and lidocaine.

Example 12

Composition Comprising Hyaluronic Acid-Hexamethylenediamine (HA-HMDA) Cross-Linked Hydrogel of the Present Invention 4 mg of hyaluronic acid (HA) having molecular weight of 1,000 kDa and 3 mg of lidocaine were added to 16 mg of the hyaluronic acid-alkylene diamine hydrogel powder prepared and dried according to the method of Example 4-1. The resultant was dissolved in 1 ml of PBS (pH 7.4) and agitated for 5 hours to obtain a composition comprising the hydrogel of the present invention, unmodified hyaluronic acid and lidocaine.

Comparative Example 1

Preparation of Hyaluronic Acid-Adipic Acid Dihydrazide (HA-ADH) Cross-Linked Hydrogel Using Adipic Acid Dihydrazide (ADH) as Cross-Linking Agent According to Hahn et al. (Hahn S K et al., Int. J. Biol. Macromol., 2007; 40; pp. 374-380), 100 mg of hyaluronic acid (HA, manufacturer: Lifecore Co.) having molecular weight of about 234 kDa was dissolved in 20 ml of water to prepare HA aqueous solution (5 mg/ml). Adipic acid dihydrazide (ADH) powder (1.736 g) in excess of a 40-fold amount as a molar ratio based on HA was added to the HA aqueous solution and completely dissolved for 10 minutes. The pH of the obtained HA/ADH mixed aqueous solution was adjusted to 4.8 by using 1 N HCl aqueous solution, and the solution was completely agitated for 30 minutes. 1-Ethyl-3-(3-dimethylaminopropyl)carbodiimide (EDC, 0.191 g) powder in excess of a 4-fold amount as a molar ratio was added thereto to activate the carboxyl group of HA with agitation. 1 N HCl aqueous solution was added to the aqueous solution to maintain pH of 4.8, and the reaction was carried out for 2 hours. After 2 hours, pH was raised to 7.0 by adding 1 N NaOH aqueous solution to halt the reaction. To reduce viscosity and impurity (uncross-linked ADH), the obtained product was sealed with a pre-washed dialysis membrane (molecular weight cut-off of 7 kDa), and was then dialyzed with 100 mM NaCl aqueous solution for 60 hours. And then, dialysis was repeated with ethanol and distilled water, respectively. After dialysis, the aqueous solution was freeze-dried for 3 days to obtain HA-ADH derivative. The obtained HA-ADH according to the above method was dissolved in 0.01 M PBS (pH 7.4) for 2 hours. Bis[sulfosuccinimidyl]suberate (BS3), which is a cross-linking agent specific for hydrazide, was dissolved in PBS, and then added to the HA-ADH solution. At this time, the adding amount of BS3 was 20 mol % of hydrazide of HA-ADH. The aqueous solution was completely mixed and was then reacted for 1 hour for a complete cross-linking reaction to obtain HA-ADH cross-linked hydrogel.

Comparative Example 2

Preparation of Hyaluronic Acid-Divinyl Sulfone (HA-DVS) Cross-Linked Hydrogel Using Divinyl Sulfone (DVS) as Cross-Linking Agent According to Oh et al. (Oh E J et al., J. Biomed. Mater. Res A., 2008; 86; pp. 685-693), 68 mg of hyaluronic acid (HA, manufacturer: Lifecore Co.) having molecular weight of about 230 kDa was dissolved in 1.68 ml of 0.2 N NaOH aqueous solution (pH 13). After complete dissolution, divinyl sulfone (DVS) was added thereto for cross-linking by reaction with the hydroxyl group of HA. At this time, the molar ratio of the hydroxyl group of hyaluronic acid and the added DVS was 1:1. The solution was reacted at 37° C. for 1 hour to obtain HA-DVS hydrogel. The prepared hydrogel was sealed with a pre-washed dialysis membrane (molecular weight cut-off of 7 kDa) and was then dialyzed with PBS for 24 hours to make ions ($Na^+$ and $OH^-$) diffusing out via dialysis membrane, and the sealed HA-DVS cross-linked product was neutralized.

Comparative Example 3

Preparation of Hyaluronic Acid-Hexamethylenediamine (HA-HMDA) Cross-Linked Hydrogel An HA-HMDA hydrogel was prepared according to the same method as Example 4 except that hyaluronic acid having molecular weight of about 1,000 kDa was used at the concentration of 3 (w/w) %, and HMDA was added as 5 mol % of the repeating unit of HA. The cross-linking rate of the prepared HA-HMDA hydrogel was 2-4%, and it was difficult for the prepared HA-HMDA hydrogel to be used as dermal filler because of too low viscoelasticity.

Comparative Example 4

Preparation of Hyaluronic Acid-Hexamethylenediamine (HA-HMDA) Cross-Linked Hydrogel An HA-HMDA hydrogel was prepared according to the same method as Example 4 except that hyaluronic acid having molecular weight of about 1,000 kDa was used at the concentration of 3.3 (w/w) %, and HMDA was added as 50 mol % of the repeating unit of HA. The cross-linking rate of the prepared HA-HMDA hydrogel was 40-45%, and it was difficult for the prepared HA-HMDA hydrogel to be used as a dermal filler because it was too dry and easily broken.

Experimental Example 1

Test for In Vitro Degradation and Swellability of Hyaluronic Acid Cross-Linked Hydrogel To anticipate in vivo persistence of hyaluronic acid cross-linked hydrogel used in the present invention, the degradation test by hyaluronic acid-degrading enzyme to the hyaluronic acid cross-linked hydrogels of Example 1, and Comparative Examples 1 and 2 was carried out.

The same mass of the hyaluronic acid cross-linked hydrogels of Example 1, and Comparative Examples 1 and 2 was incorporated into each vial. 0.2 M PBS (pH 6.2) comprising 50 U of hyaluronic acid-degrading enzyme (hyaluronidase from *Streptomyces hyalurolyticus*, Sigma-Aldrich) was added to the vials. The mixture was reacted at 37° C. for a predetermined 48 hours. Supernatant was then completely removed, and the mass of remaining hyaluronic acid cross-linked product was measured. The extent of degradation of the cross-linked product was calculated as mass ratio (%) of remaining cross-linked product and original cross-linked product. The degradation rate (%) according to elapsed time is represented in Table 1. As can be seen from Table 1, HA-DVS cross-linked product of Comparative Example 2 was completely degraded within about 25 hours, whereas the hyaluronic acid-alkylenediamine cross-linked hydrogel was only partially degraded even after 40 hours. From this result, it can be confirmed that the hyaluronic acid-alkylenediamine cross-linked hydrogel according to the present invention has in vivo persistence superior to the commercially available hydrogel.

In addition, the hyaluronic acid-alkylenediamine cross-linked hydrogel according to the present invention shows two (2) times or more swellability than the HA-ADH cross-linked product of Comparative Example 1, which shows a similar degradation rate. From this, it can be known that the hyaluronic acid-alkylenediamine cross-linked hydrogel according to the present invention is excellent filler for tissue augmentation showing high in vivo persistence and swellability.

TABLE 1

| | Weight of HA-HMDA cross-linked hydrogel of the present invention (%) | Weight of HA-ADH cross-linked hydrogel of Comparative Example 1 (%) | Weight of HA-DVS cross-linked hydrogel of Comparative Example 2 (%) |
|---|---|---|---|
| 5 hours | 190 | 110 | 200 |
| 10 hours | 180 | 105 | 160 |
| 15 hours | 160 | 102 | 115 |
| 20 hours | 135 | 100 | 70 |
| 25 hours | 115 | 88 | 0 |
| 30 hours | 100 | 78 | 0 |
| 35 hours | 88 | 72 | 0 |
| 40 hours | 67 | 60 | 0 |

Experimental Example 2

Test for In Vitro Degradation of Hyaluronic Acid Cross-Linked Hydrogel

To anticipate in vivo persistence of hyaluronic acid cross-linked hydrogel of the present invention, the degradation test by hyaluronic acid-degrading enzyme to the hyaluronic acid cross-linked hydrogels of Examples 1 to 7 was carried out.

According to Ibrahima et al. (Polymer Degradation and Stability 2007; 92: pp. 915-919), a test for in vitro degradation was carried out. The same mass of the hyaluronic acid cross-linked hydrogels of Examples 1 to 7 was incorporated into each vial. 0.2 M PBS (pH 7.4) comprising 6,080 U of hyaluronic acid-degrading enzyme (hyaluronidase from *Streptomyces hyalurolyticus*, Sigma-Aldrich) was added to the vials. The mixture was reacted at 37° C. for 2 hours. To stop the enzyme reaction, 0.8 M potassium borate (pH 9.1) was added and then heated at 100° C. for 3 minutes. To measure the amount of degradation product, N-acetylglucosamine (NAG), Ehrlich's reagent was prepared according to Reissig et al. (J. Biol. Chem.; 1955; 217: pp. 959-996). The reagent was added to the vials and reacted at 37° C. for 20 minutes. After centrifugation, the supernatant was taken, and the amount of NAG in the degraded cross-linked product was then measured with UV at the absorbance of 585 nm. To denote the extent of degradation of the cross-liked product, the degradation rate of Example 6 was set as 100%, and the degradation rates of the remaining Examples are represented in Table 2.

TABLE 2

| | HA content (mg/ml) | HA M.W. (kDa) | Amount of added cross-linking agent (mol % of HA repeating unit) | Cross-linked product (pH) | Cross-linking rate (%) | Relative degradation rate (%) |
|---|---|---|---|---|---|---|
| Ex. 1 | 10 mg/ml | 230 | 72 | 5.0-5.5 | 8-9 | 92-95 |
| Ex. 2 | 10 mg/ml | 1,000 | 72 | 5.5-5.9 | 11-13 | 78-81 |
| Ex. 3 | 15 mg/ml | 1,000 | 25 | 5.0-5.5 | 11-13 | 76-80 |
| Ex. 4 | 30 mg/ml | 1,000 | 20 | 6.0-6.5 | 10-14 | 71-73 |
| Ex. 5 | 30 mg/ml | 1,000 | 20 | 5.5-5.9 | 10-12 | 74-76 |
| Ex. 6 | 30 mg/ml | 1,000 | 10 | 6.0-6.5 | 5-7 | 100 |
| Ex. 7 | 30 mg/ml | 1,000 | 40 | 6.0-6.5 | 24-27 | 55-58 |
| Comp. Ex. 3 | 30 mg/ml | 1,000 | 5 | 6.0-6.5 | 2-4 | 120-130 |

As can be seen from Table 2, the cross-linking rate was affected by the molecular weight of HA, initial concentration and pH. If the initial concentration of HA is higher, the cross-linking rate of the cross-linked product is higher. Although the amount of added cross-linking agent is more, it was observed that the cross-linking rate is similar or even lower depending on pH. In addition, if the cross-linking rate is higher, the degradation rate is lower. Based on the above results, it can be known that a hydrogel having desired physical properties can be prepared.

Experimental Example 3

Test for Degradation Rate, Extrusion Force and Modulus of Elasticity According to Concentration of Hyaluronic Acid Cross-Linked Hydrogel This experimental example was carried out to determine optimal hydrogel preparation concentration of the composition comprising hyaluronic acid cross-linked hydrogel of the present invention. The hyaluronic acid cross-linked hydrogel of Example 4-1 was dissolved in PBS (pH 7.4) at the concentration of 1%, 1.5%, 2% and 2.4%, respectively, and agitated for 5 hours. They were charged into syringes and sterilized at 121° C. and 1.5 atm for 20 minutes. The degradation rate by hyaluronic acid-degrading enzyme, extrusion force and modulus of elasticity (G') of the sterilized compositions were measured.

TABLE 3

| Content of hydrogel in composition (3 ml syringe) (mg/ml) | Relative degradation rate (%) | Extrusion force (N) (at 27 gauge) | Modulus of elasticity (G') (Pa at 3 Hz) |
|---|---|---|---|
| 1% | 10 | 100 | 8-9 | 300 |
| 1.5% | 15 | 87 | 12-13 | 360 |
| 2% | 20 | 73 | 14-15 | 440 |
| 2.4% | 24 | 72 | 18-19 | 465 |

As can be seen from Table 3, extrusion force after sterilization was increased according to the increase of the concentration of hyaluronic acid cross-linked hydrogel. When the concentration of hydrogel was 2.0 and 2.4%, modulus of elasticity (G') was almost the same in consideration of 10% deviation of equipment, and the degradation rate was also equal. When the concentration of hydrogel was 2.4%, the extrusion force of the prepared and sterilized hydrogel was 1.3 times higher than that of 2.0% concentration. Therefore, the optimal concentration of hydrogel can be selected as 2.0%, and the combination of the desired composition can be prepared based on the above.

Experimental Example 4

Extrusion Force and Mean Particle Size after Sterilization of Composition Comprising Hyaluronic Acid Cross-Linked Hydrogel To anticipate the extrusion force of the composition comprising the hyaluronic acid cross-linked hydrogel of the present invention in accordance with a syringe and injection needle, this test was carried out.

The composition in which 18 mg of hydrogel of Example 4-9 and 2 mg of hyaluronic acid (HA) having molecular weight of about 1,000 kDa were dissolved in 1 ml of PBS (pH 7.4) and agitated for 5 hours, and the agitated compositions of Examples 8 to 12 were charged into 3 ml syringes at the same mass and humidity sterilized (121° C., 1.5 atm, 20 minutes). The mean particle size and extrusion force of each sterilized composition were measured, and the results are represented in Table 4.

Measurement of mean particle size and distribution was carried out by using a Malvern Mastersizer 2000 (Malvern Instruments Ltd., Worcestershire, UK), and 0.9% NaCl solution was used as a dispersion medium. Extrusion force was measured with 27- and 30-gauge injection needles by using an EZ-S SHIMADZU equipment. Extrusion force was measured with 1 mm/min of uniform velocity until it became 6 mm.

As can be seen from Table 4, extrusion force was affected according to the composition ratio of unmodified HA. That is, if the content of unmodified HA in the composition is higher, extrusion force is decreased by the action of unmodified HA as a lubricant. Depending on the gauge of the needle used, in the case of 3 ml syringe there was about 1.6 times difference between 30 gauge and 27 gauge. Meanwhile, the addition of lidocaine had almost no effect on extrusion force. In the case of Examples 10 and 12 in which the content of unmodified HA was high, it was observed that the composition was continuously discharged even after the application of force was stopped. In addition, in the case of the composition of Example 4-9 in which homogenization was carried out with a homogenizer and not a sieve, extrusion force was higher than that of the composition in which homogenization was carried out with a sieve. In the case of homogenizing with a homogenizer, a hydrogel having wide particle distribution was obtained. It is believed that such irregular size of hydrogel particles renders extrusion force high.

Experimental Example 5

Modulus of Elasticity after Sterilization of Composition Comprising Hyaluronic Acid Cross-Linked Hydrogel To observe the change of physical properties after sterilization of the composition comprising hyaluronic acid cross-linked hydrogel of the present invention, this test was carried out.

The composition in which 18 mg of hydrogel of Example 4-9 and 2 mg of hyaluronic acid (HA) having molecular weight of about 1,000 kDa were dissolved in 1 ml of PBS (pH 7.4) and agitated for 5 hours, and the agitated compositions of Examples 8 to 12 were charged into 3 ml syringes at the same mass and humidly sterilized (121° C., 1.5 atm, 20 minutes). The test for rheological property of each sterilized composition was carried out according to Ghosh et al. (Biomacromolecules, 2005; 6: pp. 2857-2865). The test was carried out by using an AR 2000 controlled stress rheometer (T.A. Instruments Ltd., USA), and 4-cm, 2°-cone and plate geometry to 0.1-20 Hz with 1% strain and oscillation mode. The modulus of elasticity (G') measured at 3 Hz is represented in Table 5. The deviation of equipment was ±10%, and the test was carried out at 25° C.

TABLE 4

| | Homogenization | Composition (3 ml syringe) | | | Extrusion force (N) | | Mean particle size | |
|---|---|---|---|---|---|---|---|---|
| | | Content of hydrogel (mg) | Unmodified HA (mg) | Lidocaine (mg) | 27 gauge | 30 gauge | μm | span |
| Ex. 8 | Sieve | 20 | — | — | 14-15 | 20-22 | 350 | 1.2 |
| Ex. 9 | Sieve | 18 | 2 | — | 7-8 | 11-12 | 350 | 1.2 |
| Ex. 10 | Sieve | 16 | 4 | — | 5-6 | 8-9 | 350 | 1.2 |
| Ex. 11 | Sieve | 18 | 2 | 3 | 7-8 | 11-12 | 350 | 1.2 |
| Ex. 12 | Sieve | 16 | 4 | 3 | 5-6 | 8-9 | 350 | 1.2 |
| Ex. 4-9 | Homogenizer | 18 | 2 | 3 | 8-9 | 12-13 | 350 | 1.6 |

TABLE 5

| | | Composition | | | Modulus |
| --- | --- | --- | --- | --- | --- |
| | Homogenization | Content of hydrogel (mg/ml) | Un-modified HA (mg) | Lido-caine (mg) | of elasticity (G') (Pa at 3 Hz) |
| Ex. 8 | Sieve | 20 | — | — | 440 |
| Ex. 9 | Sieve | 18 | 2 | — | 320 |
| Ex. 10 | Sieve | 16 | 4 | — | 280 |
| Ex. 11 | Sieve | 18 | 2 | 3 | 410 |
| Ex. 12 | Sieve | 16 | 4 | 3 | 360 |
| Ex. 4-9 | Homogenizer | 18 | 2 | 3 | 390 |

Figure 2:
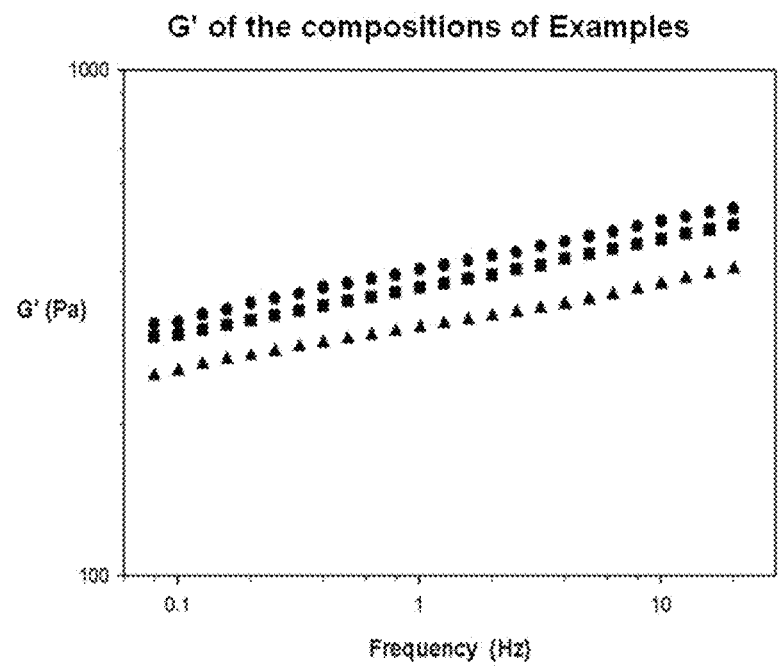
FIG. 2 is a graph representing modulus of elasticity (G') after sterilization of the HA-HMDA cross-linked hydrogel of the present invention (●: Example 8, ▲: Example 9, ■: Example 11).

As can be seen from Table 5, modulus of elasticity was affected by the composition ratio of unmodified HA. When the concentration of unmodified HA acting as a lubricant was higher, the composition having lower modulus of elasticity after sterilization was obtained. In the case of further addition of lidocaine, the modulus of elasticity of the sterilized composition was increased by about 25.6%, as compared with the composition in which only HA was added. Meanwhile, in the case that homogenization was carried out by a homogenizer (Example 4-9), modulus of elasticity was slightly (4.9%) decreased. The modulus of elasticity of the sterilized composition of Examples 8, 9 and 11 at 0.1-20 Hz is represented in FIG. 2.

Experimental Example 6

Test for Physical Property Depending on Preparation Method of Hyaluronic Acid Cross-Linked Hydrogel (Modulus of Elasticity: G')

To evaluate physical property (modulus of elasticity: G') depending on the preparation method of hyaluronic acid cross-linked hydrogel of the present invention, the modulus of elasticity after sterilization of Examples 4-1 to 4-4 was measured. The hydrogels of Examples 4-1 to 4-4 are different in that the agitation time of reaction catalysts (EDC/HOBt) is 20, 30, 40 and 60 minutes, respectively.

Each of the prepared hydrogel powders was added to PBS (pH 7.4) at the concentration of 20 mg/ml, agitated for 5 hours, charged into a 3 ml syringe and humidly sterilized (121° C., 1.5 atm, 20 minutes). The test was carried out by using an AR 2000 controlled stress rheometer (T.A. Instruments Ltd., USA), and 4-cm, 2°-cone and plate geometry to 0.1-20 Hz with 1% strain and oscillation mode. The modulus of elasticity (G') measured at 3 Hz is represented in Table 6. The deviation of equipment was ±10%, and the test was carried out at 25° C.

TABLE 6

| | Content of hydrogel (mg/ml) | Elapsed time (min) | Modulus of elasticity (G') (Pa at 3 Hz) |
| --- | --- | --- | --- |
| Example 4-1 | 20 | 20 | 440 |
| Example 4-2 | 20 | 30 | 420 |
| Example 4-3 | 20 | 40 | 300 |
| Example 4-4 | 20 | 60 | 40 |

As can be seen from Table 6, the preparation of hyaluronic acid cross-linked hydrogel was affected by the time from the dissolution of EDC/EDU to the incorporation to the reaction. The hyaluronic acid cross-linked hydrogel in which dissolution of reaction catalysts and incorporation thereof was completed within 20-30 minutes showed similar modulus of elasticity after sterilization. Contrary to this, the hyaluronic acid cross-linked hydrogel in which dissolution to incorporation took 40 minutes or more showed deterioration of physical property after sterilization. In the case of 60 minutes or more, a hydrogel having modulus of elasticity after sterilization almost as low as water was prepared. From such results, it can be known that when preparing hyaluronic acid-alkylene diamine cross-linked hydrogel the time from dissolution to incorporation of EDC/HOBt is a very important factor.

Experimental Example 7

Test for Physical Property Depending on Preparation Method of Hyaluronic Acid Cross-Linked Hydrogel (Modulus of Elasticity: G')

To evaluate physical property (modulus of elasticity: G') depending on the preparation method of hyaluronic acid cross-linked hydrogel of the present invention, the modulus of elasticity after sterilization of Examples 4-1 and 4-5 to 4-8 was measured. The hydrogels of Examples 4-1 and 4-5 to 4-8 are different in that the additional keeping times for complete cross-linking reaction are 3, 5, 7, 9 and 12 hours, respectively.

The prepared each hydrogel powder was added to PBS (pH 7.4) at the concentration of 20 mg/ml, agitated for 5 hours, charged into a 3 ml syringe and humidly sterilized (121° C., 1.5 atm, 20 minutes). The test was carried out by using an AR 2000 controlled stress rheometer (T.A. Instruments Ltd., USA), and 4-cm, 2°-cone and plate geometry to 0.1-20 Hz with 1% strain and oscillation mode. The modulus of elasticity (G') measured at 3 Hz is represented in Table 6. The deviation of equipment was ±10%, and the test was carried out at 25° C.

TABLE 7

| | Content of hydrogel (mg/ml) | Additional keeping time (45° C.) (hour) | Modulus of elasticity (G') (Pa at 3 Hz) |
| --- | --- | --- | --- |
| Example 4-1 | 20 | 10 | 440 |
| Example 4-5 | 20 | 3 | 300 |
| Example 4-6 | 20 | 5 | 350 |
| Example 4-7 | 20 | 7 | 380 |
| Example 4-8 | 20 | 9 | 425 |

As can be seen from Table 7, if the keeping time is increased, the modulus of elasticity after sterilization of the composition is increased, and in the case of 9 hours or more, almost the same modulus of elasticity was shown. From this, it was verified that in the case of keeping at the above temperature for 9 hours or longer, the hydrogel having good modulus of elasticity even after sterilization can be prepared by processing cross-linking reaction completely and sufficiently. From the above results, it can be known that at the time of preparing the hyaluronic acid-alkylene diamine cross-linked product it is important to keep the reaction for a certain time or more for a complete cross-linking reaction.

Experimental Example 8

Removal of Unreacted Materials Depending on Purification Method of Hyaluronic Acid Cross-Linked Hydrogel To evaluate the difference of removal of unreacted materials depending on the preparation method of the hyaluronic acid cross-linked hydrogel of the present invention, the remaining unreacted materials in the hyaluronic acid cross-linked hydrogel prepared in Examples 4-1 and 4-10 were analyzed by using liquid chromatography. Samples were treated with a hyaluronic acid-degrading enzyme (Hase) to degrade. Unreacted materials of HMDA were quantitatively analyzed by using a $C_{18}$-column, ACN/0.1% TFA as a mobile phase and a UV detector. Unreacted materials of EDC and HOBt were analyzed by using a GPC column, 20 mM sodium phosphate (pH 7.6) as a mobile phase and a UV detector. In the case of HMDA and EDC, it was confirmed that unreacted materials were controlled to below the detection limit (2 ppm) in both the hydrogel of Example 4-10 in which unreacted materials were removed by using a dialysis membrane and the hydrogel of Example 4-1 in which unreacted materials were removed by using ethanol and a buffer. However, in the case of HOBt, unreacted materials were below the detection limit (2 ppm) in the hydrogel of Example 4-1, but 10 times the amount of HOBt was detected in the hydrogel of Example 4-10 in which unreacted materials were removed by using a dialysis membrane. It is believed that such a difference resulted from the fact that HOBt has a tendency to more easily dissolve in organic solvent so that it is not well purified by a dialysis method.

Experimental Example 9

Test for Persistence Effect of Hyaluronic Acid Cross-Linked Hydrogel of the Present Invention Depending on In Vitro Degradation and Physical Property (G')

Figure 3:
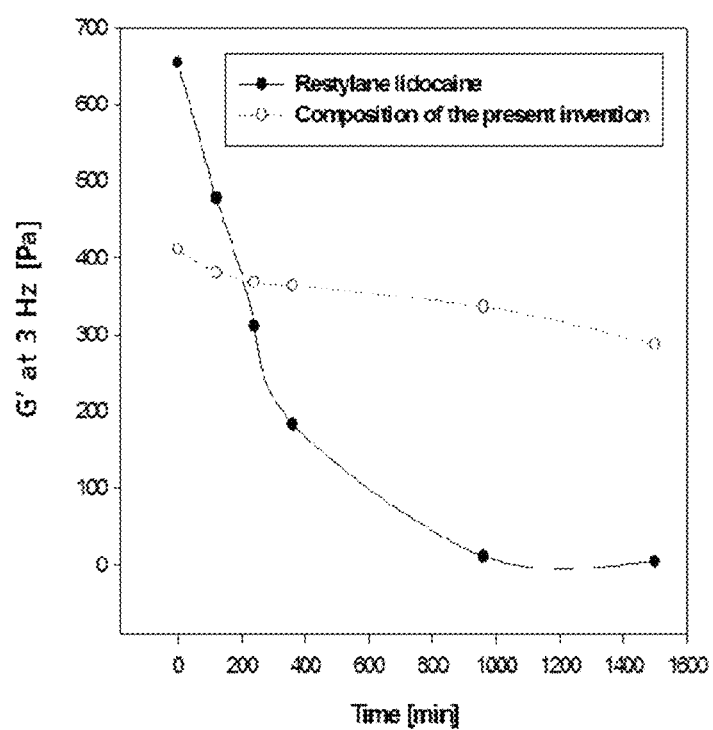
FIG. 3 is a graph representing the degradation of the sterilized composition comprising the HA-HMDA cross-linked hydrogel of the present invention and Comparative Product (Restylane® Lidocaine) by hyaluronidase in connection with the modulus of elasticity (G') (○: Example 11, ●: Comparative Product).

The sensitivity of the sterilized composition comprising the hyaluronic acid cross-linked hydrogel according to the present invention to a hyaluronic acid-degrading enzyme was evaluated in comparison with commercially available filler for tissue augmentation, Restylane® Lidocaine, in connection with G' value. To observe the extent of degradation according to elapse of time in connection with G' value, 800 μl of the sterilized composition of Example 11 and Restylane® Lidocaine were dispensed into a 1.5 ml test tube. Hyaluronic acid-degrading enzyme (Hase, *Bovine Testes*, Sigma-Aldrich) was dissolved in PBS (pH 7.4) at the concentration of 2 mg/ml (2,000 U) and 15 μl of the enzyme solution was dispensed into each test tube. After reaction at 37° C. for each predetermined time, the modulus of elasticity (G') was measured at 3 Hz. The change of modulus of elasticity (G') is represented in FIG. 3. The initial modulus of elasticity at 3 Hz of Restylane® Lidocaine is 620 Pa, and that of the sterilized composition of Example 11 is 410 Pa. The change of modulus of elasticity was checked over 25 hours. As can be seen from FIG. 3, in the case of Restylane® Lidocaine the initial modulus of elasticity is high, but it is rapidly degraded by hyaluronic acid-degrading enzyme until 3 hours to show a very low modulus of elasticity. Contrary to this, the sterilized composition of Example 11 showed stability to degradation even until 25 hours. In addition, it was confirmed that the degradation of cross-linked hyaluronic acid (HA) has no relation to the initial modulus of elasticity (G').

Experimental Example 10

Test for Tissue Augmentation (Wrinkle Improvement) Effect and Biocompatibility of Hyaluronic Acid Cross-Linked Hydrogel of the Present Invention The tissue augmentation effect and biocompatibility of the hyaluronic acid cross-linked hydrogel of the present invention were evaluated by comparison with a commercially available filler for tissue augmentation (wrinkle improvement), Restylane®.

Tissue Augmentation (Wrinkle Improvement) Effect

According to Fujimura et al. (Fujimura T et al., J. Dermatol. Sci., 2000; 24; pp. 105-111), the back of a six-week-old female hairless mouse (type SKH, Jung-Ang Lab Animal Inc., Korea) was tattooed with a rectangle (1.5×1.5 $cm^2$) to measure the wrinkle-induced surface area, and 0.2 μg of calcitriol (in ethanol) was applied once a day, six times per week for 4 weeks to artificially induce wrinkles. On day 3 after stopping the application of wrinkle inducer, the hyaluronic acid cross-linked hydrogel of the present invention and commercially available Restylane® as a control were injected into the dorsal subcutaneous layer of the mouse within the rectangle tattoo where wrinkles were induced. As the hyaluronic acid cross-linked hydrogel of the present invention, the hyaluronic acid cross-linked hydrogel of Examples 2, 3, 4 and 5 were homogenized by a homogenizer (T-18 basic, IKA, Tokyo, Japan) at 8,000 rpm for 5 minutes, and 0.4 ml of each hydrogel was then injected into the dorsal subcutaneous layer of the wrinkle-induced mouse within the rectangular tattoo by using a 30-gauge needle. As a positive control, 0.4 ml of Restylane® (Manufacturer: Q-Med AB; 20 mg/ml) was injected by using a 30-gauge needle. To analyze the extent of wrinkle improvement, photographs were taken at the same distance and light, and the mean of wrinkle improvement area was then calculated by using an image analyzer (Artimage 2 software).

Three (3) mice were used as a control group and a test group, respectively, and each wrinkle improvement area was calculated and an average was taken. To evaluate the extent of wrinkle improvement, the surface of the mice's dorsal rectangular tattoos was analyzed by using an image analyzer once a week for eleven (11) weeks.

The wrinkle improvement area according to the elapse of time is represented in Table 8. As can be seen from Table 8, the positive control group in which Restylane® was treated after wrinkle induction, and the groups in which HA-HMDA cross-linked hydrogels of Examples 2 and 3 were treated showed remarkable wrinkle improvement effect as compared with the negative control group in which none was treated after wrinkle induction.

TABLE 8

|  | Wrinkle improvement area of normal group ($cm^3$) | Wrinkle improvement area of negative control group ($cm^3$) | Wrinkle improvement area of Restylane ® treated group ($cm^3$) | Wrinkle improvement area of Example 2 hydrogel treated group ($cm^3$) | Wrinkle improvement area of Example 3 hydrogel treated group ($cm^3$) |
| --- | --- | --- | --- | --- | --- |
| 0 | 3.100 | 2.300 | 2.300 | 2.400 | 2.400 |
| 1 week | 3.100 | 2.400 | 3.000 | 3.100 | 3.000 |
| 2 week | 3.100 | 2.400 | 3.100 | 3.100 | 3.000 |
| 3 week | 3.010 | 2.500 | 3.100 | 3.200 | 3.100 |

TABLE 8-continued

| | Wrinkle improvement area of normal group (cm³) | Wrinkle improvement area of negative control group (cm³) | Wrinkle improvement area of Restylane ® treated group (cm³) | Wrinkle improvement area of Example 2 hydrogel treated group (cm³) | Wrinkle improvement area of Example 3 hydrogel treated group (cm³) |
|---|---|---|---|---|---|
| 4 week | 3.000 | 2.500 | 3.100 | 3.200 | 3.100 |
| 5 week | 3.060 | 2.464 | 3.010 | 3.194 | 3.299 |
| 6 week | 3.100 | 2.466 | 2.900 | 3.200 | 3.300 |
| 7 week | 3.060 | 2.511 | 3.011 | 3.285 | 3.270 |
| 8 week | 3.060 | 2.534 | 2.944 | 3.285 | 3.269 |
| 9 week | 3.050 | 2.564 | 2.964 | 3.275 | 3.260 |
| 10 week | 3.041 | 2.664 | 2.998 | 3.272 | 3.260 |
| 11 week | 3.040 | 2.634 | 2.999 | 3.273 | 3.260 |

Figure 4:
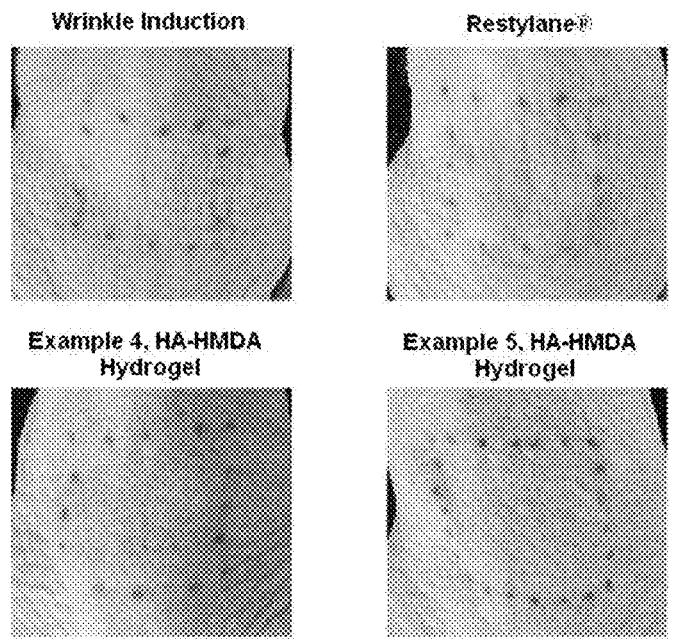
FIG. 4 is photographs for observing the improvement of dorsal epidermal wrinkle of wrinkle-induced negative control mouse, Restylane®-treated positive control mouse, and the present hydrogels of Examples 4 and 5-treated mouse on week 11 after sample administration.

Up to 4 weeks, all the groups in which Restylane® and the hydrogels of Examples 2 and 3 were treated showed similar wrinkle improvement effect. However, after 4 weeks, according to the elapse of time the groups in which the HA-HMDA cross-linked hydrogels of the present invention were treated showed higher wrinkle improvement effect than the positive control group in which Restylane® was treated. In addition, the HA-HMDA cross-linked hydrogels of Examples 4 and 5 showed a level of wrinkle improvement effect similar to the hydrogels of Examples 2 and 3. FIG. 4 is photographs showing the status of dorsal epidermis of a wrinkle-induced negative control hairless mouse, a Restylane®-treated positive control hairless mouse, and the HA-HMDA hydrogels of Examples 4 and 5-treated hairless mice, 11 weeks after sample administration. As can be seen from Table 8 and FIG. 4, the composition comprising the HA-HMDA hydrogel of the present invention showed a wrinkle improvement effect superior to that of Restylane®.

Biocompatibility

Figure 5:
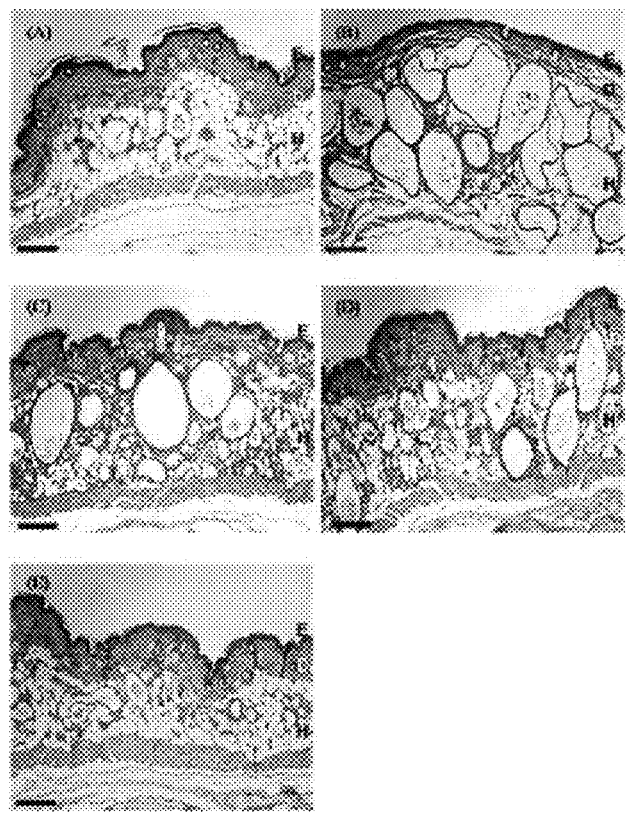
FIG. 5 is optical microscope photographs of dermal tissue specimens of each group after H&E staining to compare effects of the composition comprising the HA-HMDA cross-linked hydrogel of the present invention on tissues with control groups, and the marked bar represents 20 nm ((A): normal group, (B): wrinkle-induced negative control group, (C): Restylane® treated positive control group, (D): HA-HMDA hydrogel of Example 2 treated group, (E): HA-HMDA hydrogel of Example 3 treated group, E: epidermis, D: dermis, H: hypoderm).

On week 12 after administration of hyaluronic acid cross-linked hydrogel, a histological test was carried out by using hematoxylin-eosin (H&E) staining. Skin samples were taken from each mouse, and the skin samples were then fixed with 10% (v/v) buffered formaldehyde, dehydrated with ethanol, embedded in paraffin to make specimens, sectioned at the thickness of 4 nm, and stained with H&E. Photographs of the stained specimens were taken with an optical microscope and are represented in FIG. 5. As can be seen from FIG. 5, the mouse administered with the hydrogel of Example showed no inflammation reaction—the same as a control mouse in which wrinkles were not induced (in case of H&E, hematoxylin is stained in blue at the inflammation reaction, and eosin is stained in red as a counter-staining).

Meanwhile, when the wrinkle-induced negative control group (5B) is compared with the normal group (5A), it can be known that epidermis (E) was flattened out, and dermis (D) was thickened and became rough due to skin impairment according to wrinkle induction.

On the other hand, in the case of the treatment of HA-HMDA cross-linked hydrogel of Examples 2 and 3 (FIGS. 5D and 5E), evident improvement effect at the epidermis, dermis and hypoderm was observed, and the epidermis was changed in a way similar to the normal group. In the case of dermis, the wrinkle-induced negative control group and the Restylane®-treated positive control group showed some inflammation reaction, but the hydrogel of the present invention-treated groups showed no hemolysis or inflammation reaction, the same as the normal mouse group, and dermal tissue was regenerated. The thickness of the regenerated dermis was the same as that of the Restylane®-treated positive control group and the wrinkle-not-induced control group. The augmentation of dermal thickness as above can efficiently contribute to tissue augmentation. In the case of hypodermal tissue, lumen of the hypodermal tissue was remarkably dilated in the wrinkle-induced negative control group and the Restylane®-treated positive control group, whereas lumen of the hypodermal tissue regenerated by injecting HA-HMDA cross-linked hydrogel of Example 3 was regenerated in almost the same shape as that of the hypodermal tissue of the wrinkle-not-induced control group.

Example 10-1

The tissue augmentation effect and biocompatibility of the hyaluronic acid cross-linked hydrogel of the present invention were evaluated by comparison with a commercially available filler for tissue augmentation (wrinkle improvement), Restylane® Lidocaine.

Tissue Augmentation (Wrinkle Improvement) Effect

According to Fujimura et al. (Fujimura T et al., J. Dermatol. Sci., 2000; 24; pp. 105-111), the back of a six-week-old female hairless mouse (type SKH, Jung-Ang Lab Animal Inc., Korea) was tattooed with a rectangle (1.5×1.5 cm²) to measure wrinkle-induced surface area, and 0.2 μg of calcitriol (in ethanol) was applied once a day, six times per week for 4 weeks to artificially induce wrinkles. On day 3 after stopping the application of wrinkle inducer, 0.4 ml of the hyaluronic acid cross-linked hydrogel of Example 11 was injected into the dorsal subcutaneous layer of the wrinkle-induced mouse within the rectangular tattoo by using a 3 ml syringe and a 27-gauge needle. As a positive control, 0.4 ml of Restylane® Lidocaine (Manufacturer: Q-Med AB; 20 mg/ml) was injected by using a 27-gauge needle.

Figure 6:
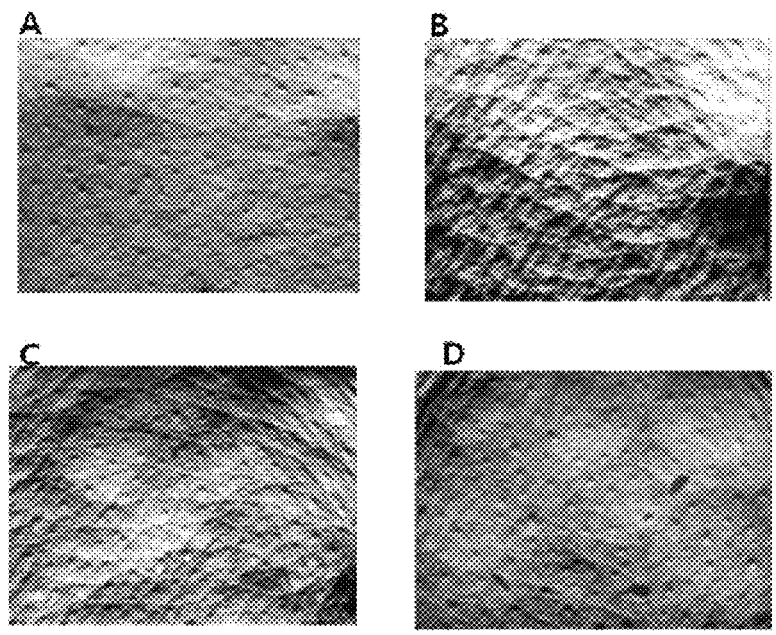
FIG. 6 is images of replicas of each mouse group on week 13 after sample administration (A: normal group, B: wrinkle-induced negative control group, C: Restylane® Lidocaine treated positive control group, D: HA-HMDA hydrogel of Example 11 treated group).
Figure 7:
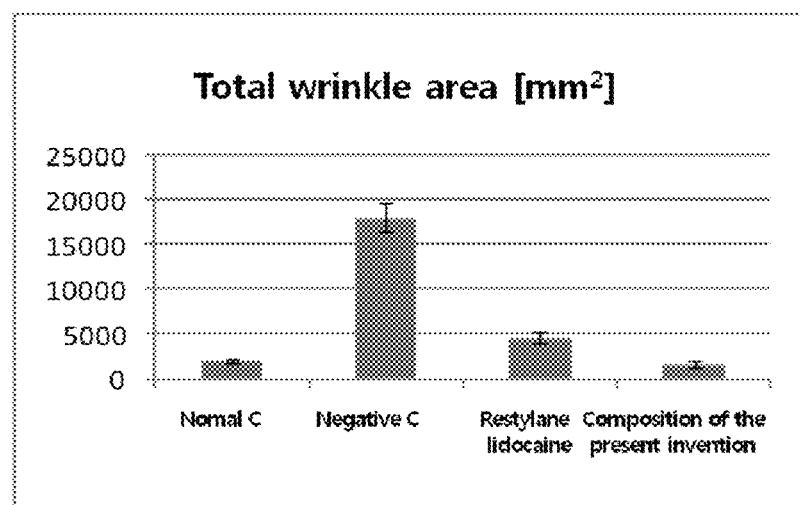
FIG. 7 shows the results of analyzing images of replicas of each mouse group on week 13 after sample administration by using Visioline® (Normal C: normal group, Negative C: wrinkle-induced negative control group).

Seven (7) mice were used as a normal group, negative/positive control groups and a test group, respectively. After thirteen (13) weeks of observation, replicas of dermal skin formed by wrinkles were made by using silicone-based replicating resin (Silflo, Flexico Development Ltd., UK), and the wrinkle improvement area was measured and calculated by using an image analyzer (Visioline SV650, CK Electronics, Germany) and an average was taken. Images of replicas of the mice's dorsal rectangular tattoo are represented in FIG. 6. As can be seen from FIG. 6, the mouse treated with the sterilized composition comprising the HA-HMDA cross-linked hydrogel of Example 11 showed remarkable wrinkle improvement effect as compared with the mouse which was not treated after wrinkle induction (B). It is believed that such remarkable tissue augmentation (wrinkle improvement) effect is derived from excellent swellability, and dermal and hypodermal regeneration effects of the sterilized composition comprising the HA-HMDA cross-linked hydrogel of the present invention. In addition, the results of the wrinkle area obtained from the analysis of the replicas by using Visioline are represented in FIG. 7. As can be seen from FIGS. 6 and 7, the hairless mouse treated with the sterilized composition comprising the HA-HMDA cross-linked hydrogel of the present invention showed remarkably improved wrinkles of dorsal epidermis almost the same as the normal group, and showed superior wrinkle improvement effect to Restylane® Lidocaine.

Biocompatibility

Figure 8:
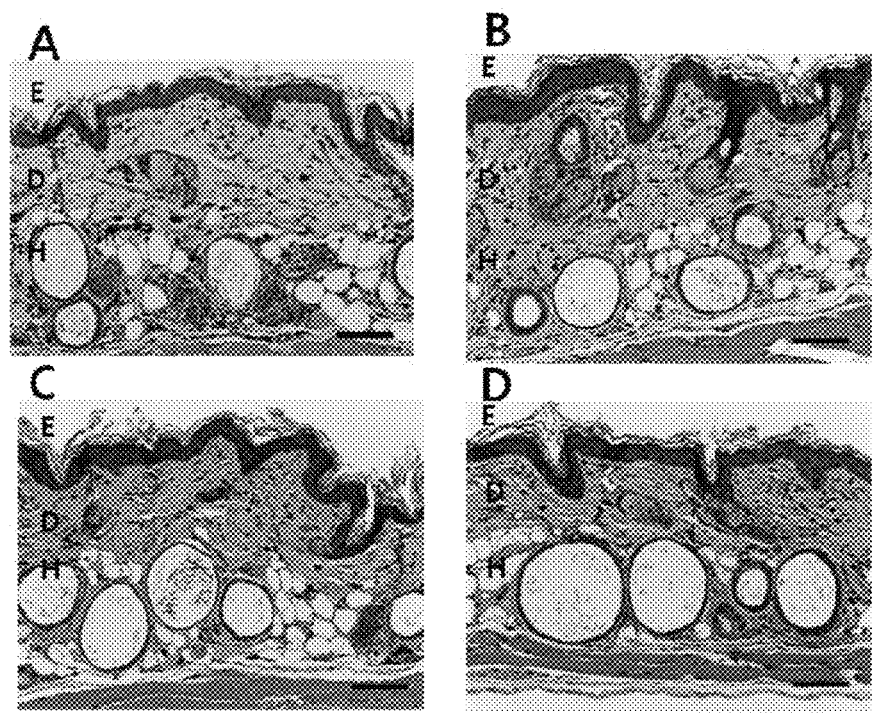
FIG. 8 is optical microscope photographs of dermal tissue specimens of each group after H&E staining to compare the effects of the composition comprising the HA-HMDA cross-linked hydrogel of the present invention on tissues with control groups, and the marked bar represents 100 nm (A: normal group, B: wrinkle-induced negative control group, C: Restylane® Lidocaine treated positive control group, D.

On week 14 after administration of hyaluronic acid cross-linked hydrogel, a histological test was carried out by using hematoxylin-eosin (H&E) staining Skin samples were taken from each mouse, and the skin samples were then fixed with 10% (v/v) buffered formaldehyde, dehydrated with ethanol, embedded in paraffin to make specimens, sectioned at the thickness of 4 μm, and stained with H&E. Photographs of the stained specimens were taken with an optical microscope and are represented in FIG. 8. The mouse administered with the sterilized hydrogel composition of Example 11 showed no inflammation reaction, the same as a control mouse in which wrinkles were not induced (in case of H&E, hematoxylin is stained in blue at the inflammation reaction, and eosin is stained in red as a counter-staining).

Meanwhile, when the wrinkle-induced negative control group (B) is compared with the normal group (A), it can be known that epidermis (E) was flattened out, and dermis (D) was thickened and became rough due to skin impairment according to wrinkle induction. Contrary to this, in the case of the treatment of the sterilized composition comprising the HA-HMDA cross-linked hydrogel of the present invention (D), evident improvement effect at the epidermis, dermis and hypoderm was observed, and the epidermis was changed in a way similar to the normal group. In the case of dermis, the wrinkle-induced negative control group and the Restylane® Lidocaine-treated positive control group showed some inflammation reaction, but the hydrogel of the present invention-treated groups showed no hemolysis or inflammation reaction, the same as the normal mouse group, and dermal tissue was regenerated. The thickness of the regenerated dermis was the same as that of the Restylane® Lidocaine treated positive control group and the normal group. The augmentation of dermal thickness as above can efficiently contribute to tissue augmentation. In the case of hypodermal tissue, lumen of the hypodermal tissue was remarkably dilated in the wrinkle-induced negative control group and the Restylane® Lidocaine-treated positive control group, whereas lumen of the hypodermal tissue regenerated by injecting the sterilized composition of Example 11 was regenerated in almost the same shape as that of the hypodermal tissue of the normal group.

From the above results, it can be known that the hydrogel of hyaluronic acid cross-linked with alkylene diamine and the sterilized hydrogel of the present invention have excellent biocompatibility and tissue augmentation (wrinkle improvement effect) due to proper swellability and regeneration of dermal and hypodermal tissues, and can be efficiently used as a filler for tissue augmentation since they persist in the body much longer than commercially available fillers for tissue augmentation.

The invention claimed is:

1. A filler composition for tissue augmentation comprising from 1 to 3% (w/w) of a hydrogel of hyaluronic acid cross-linked with an alkylene diamine having the following Formula 1 and from 0.1 to 0.4% (w/w) of an unmodified hyaluronic acid, based on total weight of the composition:

[HA]-C(O)—NH—R1-NH—C(O)-[HA]   [Formula 1]

wherein, HA represents hyaluronic acid excluding one carboxyl group or a salt thereof, R1 represents $C_3$-$C_{10}$ alkylene unsubstituted or substituted with hydroxy, $C_1$-$C_6$ alkyl or $C_1$-$C_6$ alkoxy, and the molecular weight of the hyaluronic acid used in a cross-linking reaction is from 10,000 to 4,000,000 Daltons, and the molecular weight of unmodified hyaluronic acid is from 10,000 to 4,000,000 Daltons.

2. The composition according to claim 1, further comprising lidocaine.

3. The composition according to claim 1, wherein the molecular weight of the hyaluronic acid is from 20,000 to 4,000,000 Daltons.

4. The composition according to claim 1, wherein the alkylene diamine is hexamethylenediamine.

5. The composition according to claim 1, wherein the hyaluronic acid cross-linked with alkylene diamine is prepared by reacting a hyaluronic acid with a $C_3$-$C_{10}$ alkylene diamine compound unsubstituted or substituted with hydroxy, $C_1$-$C_6$ alkyl or $C_1$-$C_6$ alkoxy in the presence of a carboxyl-activating agent and a peptide bond catalyst at a pH of from 5.5 to 6.5.

6. The composition according to claim 1, wherein the cross-linked hydrogel has a degree of cross linking of from 5 to 35%.

7. The composition according to claim 1 for the removal or improvement of skin wrinkles.

8. The composition according to claim 1 for the enlargement of the volume of a body part selected from the group consisting of a cheek, a lip, a breast and a hip.

9. A method for preparing the composition of claim 1 comprising the steps of:
    a. reacting hyaluronic acid with a $C_3$-$C_{10}$ alkylene diamine compound unsubstituted or substituted with hydroxy, $C_1$-$C_6$ alkyl or $C_1$-$C_6$ alkoxy in the presence of a carboxyl-activating agent and a peptide bond catalyst to prepare a hydrogel of hyaluronic acid cross-linked with alkylene diamine;
    b. homogenizing the prepared hydrogel;
    c. removing unreacted materials; and
    d. adding an unmodified hyaluronic acid thereto.

10. The method according to claim 9, wherein the carboxyl-activating agent and the peptide bond catalyst are dissolved in water and added to a mixture of hyaluronic acid and alkylene diamine compound within 30 minutes.

11. The method according to claim 9, wherein the hydrogel of hyaluronic acid cross-linked with alkylene diamine is prepared by maintaining the reaction mixture in step (a) at from 30° C. to 50° C. for 9 hours or more without agitation.

12. The method according to claim 9, wherein the hydrogel of hyaluronic acid cross-linked with alkylene diamine is prepared at a pH of from 5.5 to 6.5.

* * * * *